US012274801B2

(12) United States Patent
Augustin

(10) Patent No.: US 12,274,801 B2
(45) Date of Patent: Apr. 15, 2025

(54) SPIROMETER STERILIZING ASSEMBLY

(71) Applicant: Delcina Augustin, San Francisco, CA (US)

(72) Inventor: Delcina Augustin, San Francisco, CA (US)

( * ) Notice: Subject to any disclaimer, the term of this patent is extended or adjusted under 35 U.S.C. 154(b) by 583 days.

(21) Appl. No.: 17/709,084

(22) Filed: Mar. 30, 2022

(65) Prior Publication Data

US 2023/0310670 A1    Oct. 5, 2023

(51) Int. Cl.
*A61L 2/10* (2006.01)
*A61B 5/087* (2006.01)
*A61B 5/097* (2006.01)
*A61L 2/28* (2006.01)

(52) U.S. Cl.
CPC ............... *A61L 2/10* (2013.01); *A61B 5/087* (2013.01); *A61B 5/097* (2013.01); *A61L 2/28* (2013.01); *A61L 2202/11* (2013.01); *A61L 2202/24* (2013.01)

(58) Field of Classification Search
CPC ........................................................ A61L 2/10
See application file for complete search history.

(56) References Cited

U.S. PATENT DOCUMENTS

| | | | |
|---|---|---|---|
| 5,570,702 A | 11/1996 | Forman | |
| 6,461,568 B1 | 10/2002 | Eckhardt | |
| D504,947 S | 5/2005 | McAuley | |
| 7,888,656 B2 | 2/2011 | Freedgood | |
| 9,839,707 B2 | 12/2017 | Won | |
| 2005/0236579 A1 | 10/2005 | Jenkins | |
| 2006/0242788 A1 | 11/2006 | Day | |
| 2018/0353809 A1* | 12/2018 | Pancholy | A61L 2/232 |
| 2019/0125907 A1* | 5/2019 | Dobrinsky | B65D 51/24 |

FOREIGN PATENT DOCUMENTS

WO    WO2016003967    1/2016

* cited by examiner

*Primary Examiner* — Kevin Joyner

(57) ABSTRACT

A spirometer sterilizing assembly for sterilizing a mouthpiece of a spirometer includes a spirometer that has a mouthpiece which can be placed in a user's mouth. A cover is positionable around the mouthpiece and the cover is comprised of a fluid impermeable material to protect the mouthpiece from contamination when the cover is positioned around the mouthpiece. A sterilizing unit is provided and the sterilizing unit is integrated into the cover. The sterilizing unit emits ultraviolet radiation when the sterilizing unit is turned on to kill microbes on the mouthpiece to sterilize the mouthpiece between uses.

6 Claims, 5 Drawing Sheets

SPIROMETER STERILIZING ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to sterilizing devices and more particularly pertains to a new sterilizing device for sterilizing a mouthpiece of a spirometer. The device includes a spirometer that has a mouthpiece and a cover that is positionable around the mouthpiece. The device includes a plurality of light emitters that each emits ultraviolet light into an interior of the cover to sterilize the mouthpiece when the mouthpiece is inserted into the cover.

(2) Description of Related Art Including Information Disclosed Under 37 CFR 1.97 and 1.98

The prior art relates to sterilizing devices including a prophylactic device that is positionable around a mouthpiece to inhibit direct contact between a user's mouth and the mouthpiece. The prior art discloses a variety of devices that emit ultraviolet light for the purposes of sterilization. The prior art discloses a variety of methods of employing ultraviolet light for the purposes of sterilization. The prior art discloses a case that can be closed around a dental device and which includes ultraviolet light emitters for sterilizing the dental device. In no instance does the prior art discloses a spirometer with a mouthpiece and a cover that is positionable around the mouthpiece which includes ultraviolet light emitters for sterilizing the mouthpiece.

BRIEF SUMMARY OF THE INVENTION

An embodiment of the disclosure meets the needs presented above by generally comprising a spirometer that has a mouthpiece which can be placed in a user's mouth. A cover is positionable around the mouthpiece and the cover is comprised of a fluid impermeable material to protect the mouthpiece from contamination when the cover is positioned around the mouthpiece. A sterilizing unit is provided and the sterilizing unit is integrated into the cover. The sterilizing unit emits ultraviolet radiation when the sterilizing unit is turned on to kill microbes on the mouthpiece to sterilize the mouthpiece between uses.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
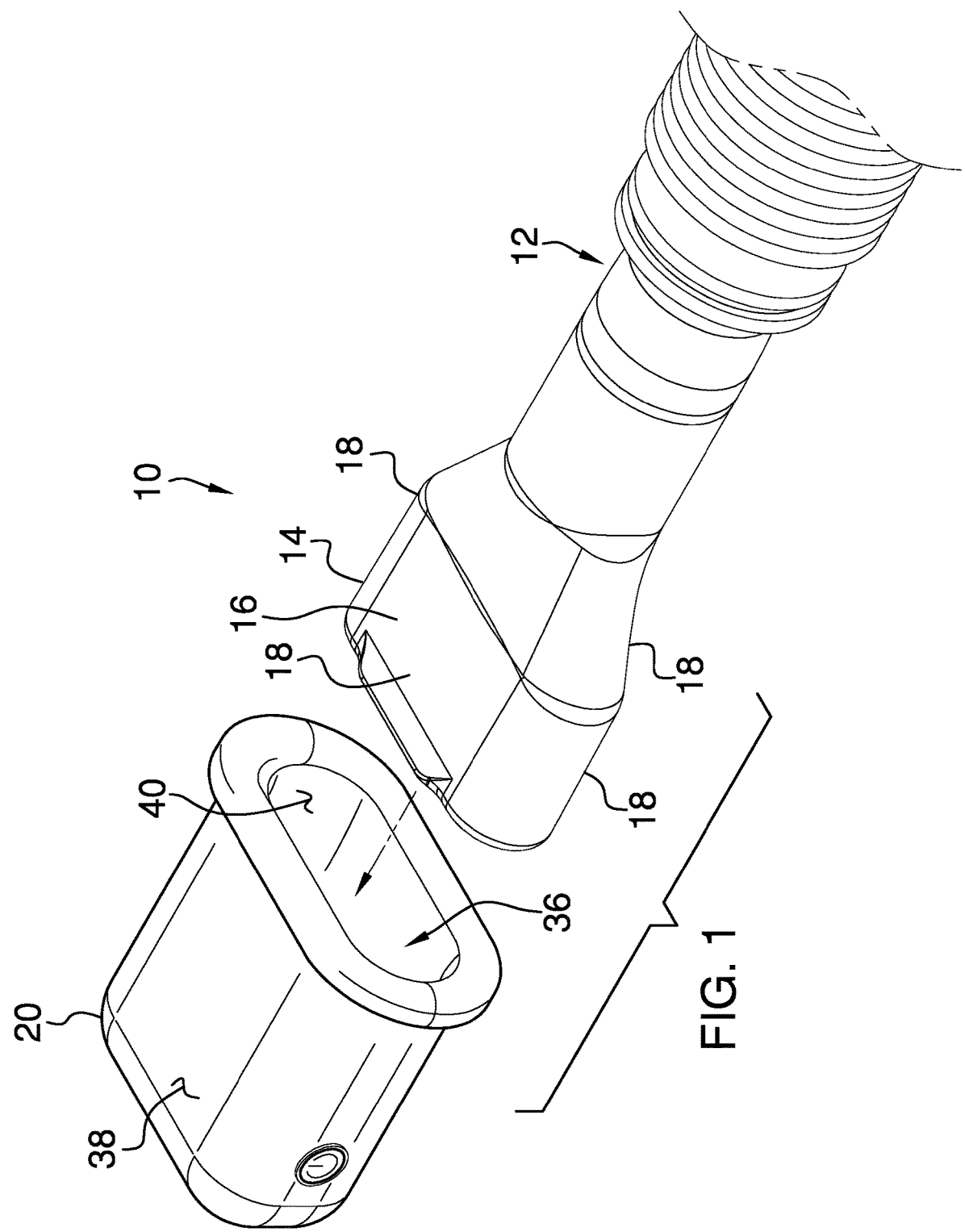
FIG. 1 is an exploded perspective view of a spirometer sterilizing assembly according to an embodiment of the disclosure.
Figure 2:
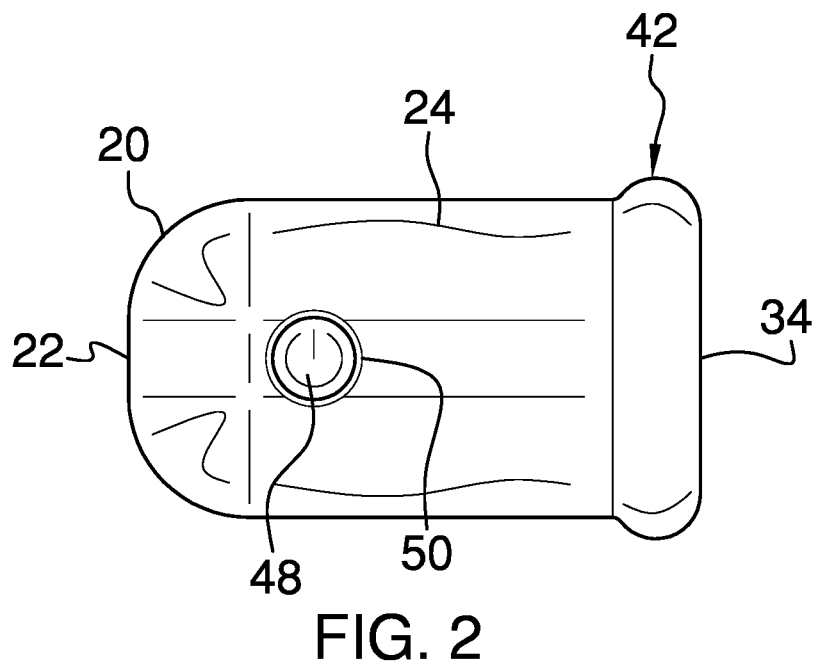
FIG. 2 is a right side view of a cover of an embodiment of the disclosure.
Figure 3:
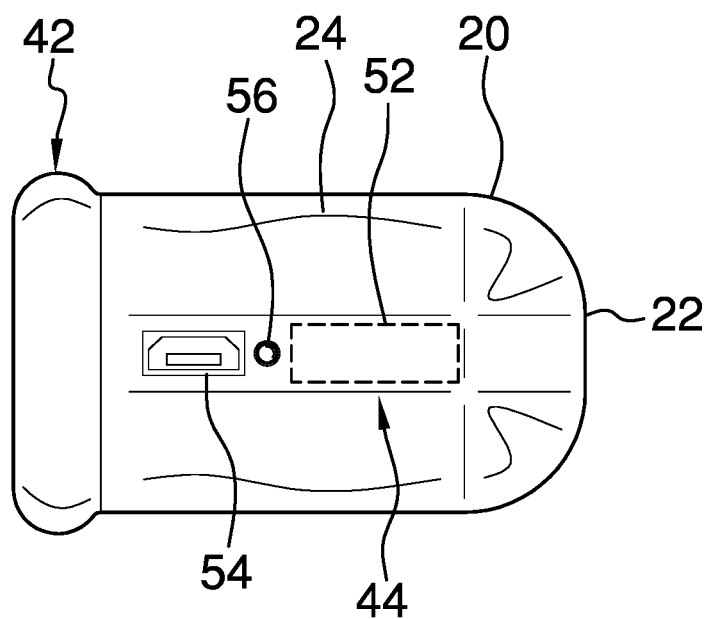
FIG. 3 is a left side phantom view of a cover of an embodiment of the disclosure.
Figure 4:
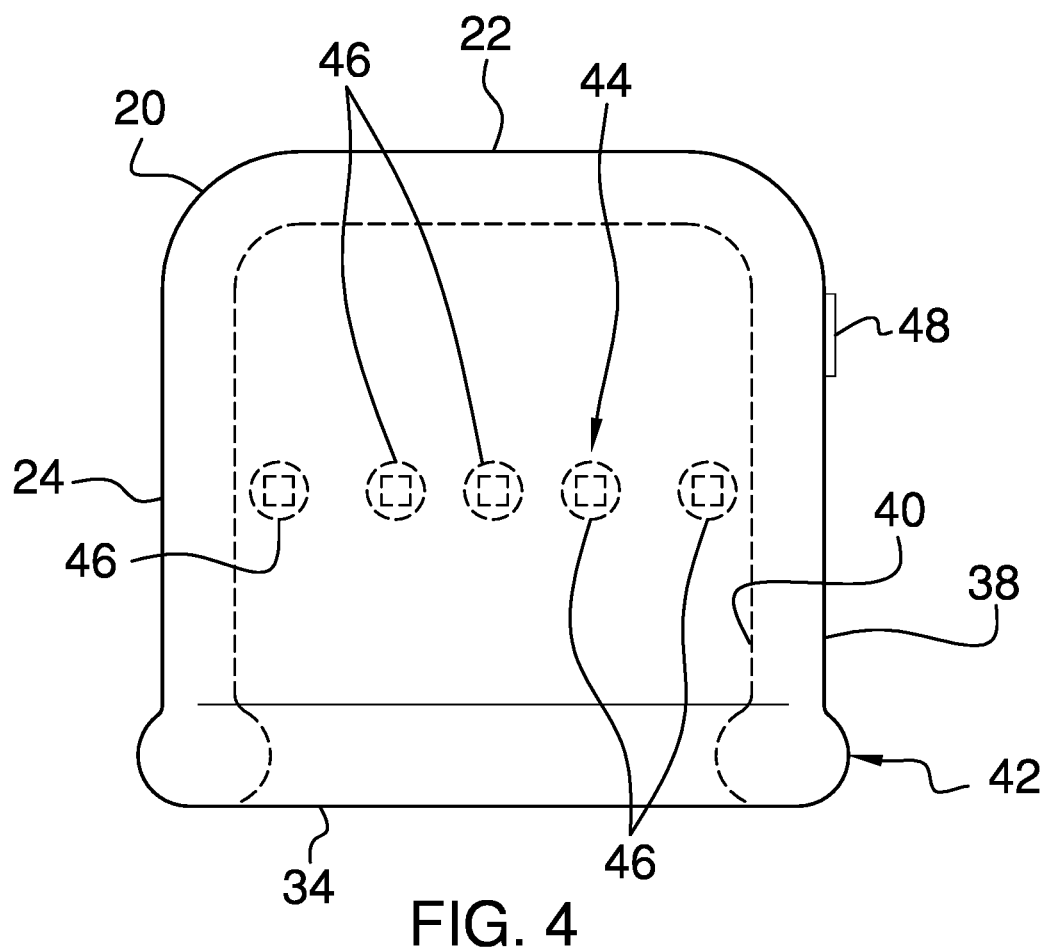
FIG. 4 is a top phantom view of a cover of an embodiment of the disclosure.
Figure 5:
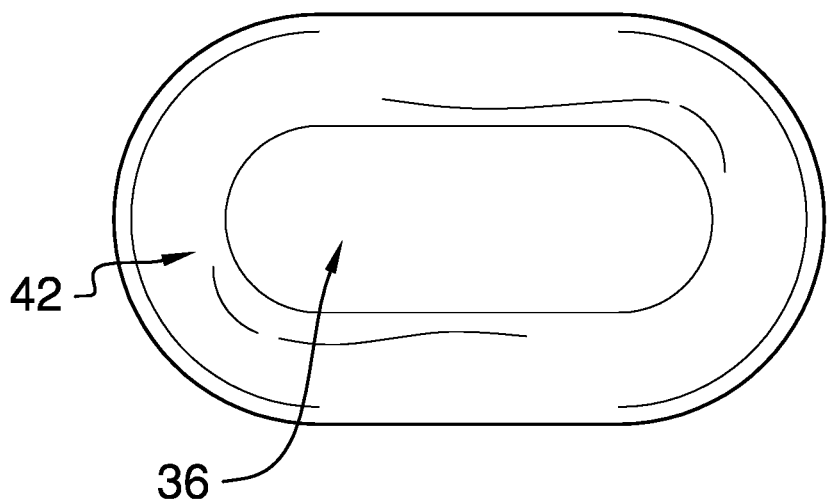
FIG. 5 is a front view of a cover of an embodiment of the disclosure.
Figure 6:
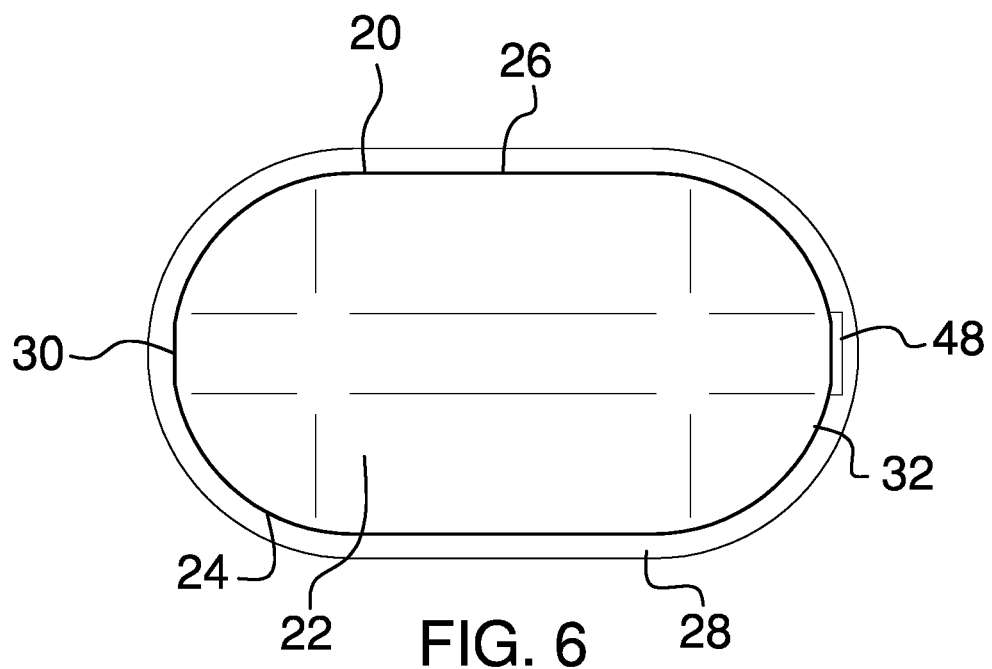
FIG. 6 is a back view of a cover of an embodiment of the disclosure.
Figure 7:
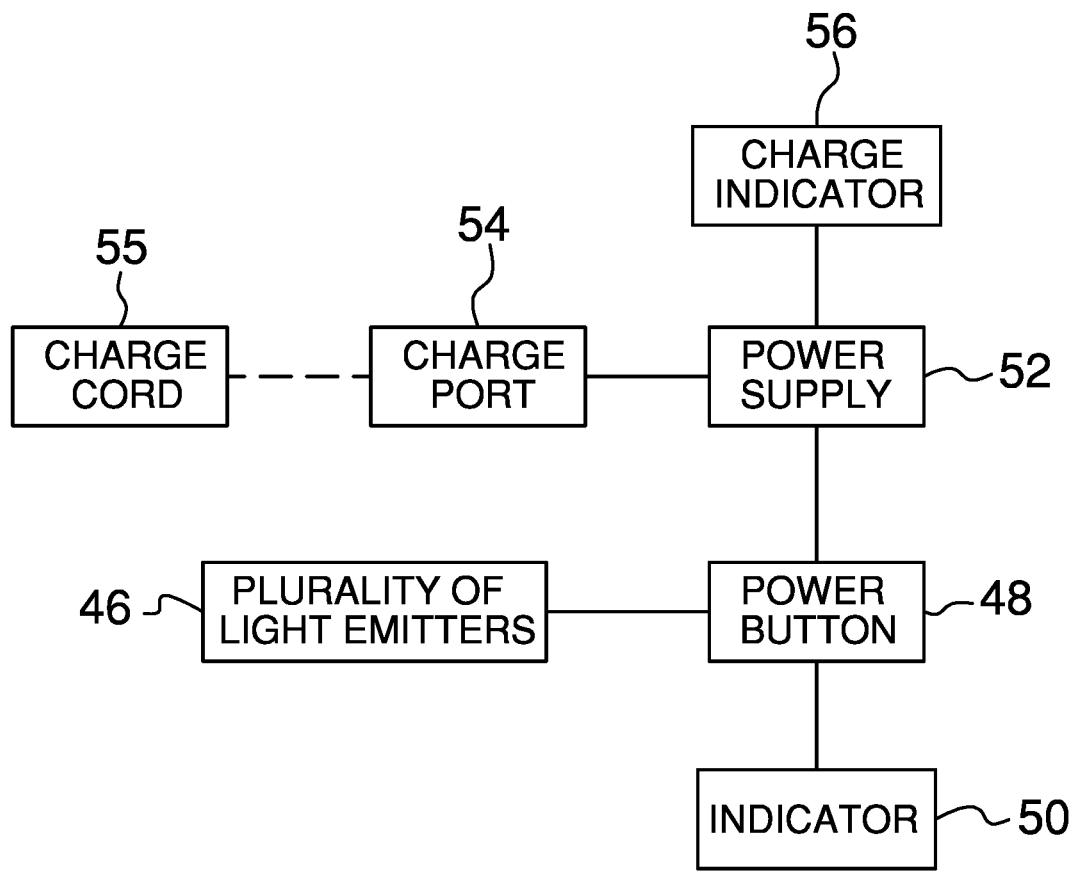
FIG. 7 is a schematic view of an embodiment of the disclosure.

With reference now to the drawings, and in particular to FIGS. 1 through 7 thereof, a new sterilizing device embodying the principles and concepts of an embodiment of the disclosure and generally designated by the reference numeral 10 will be described.

As best illustrated in FIGS. 1 through 7, the spirometer sterilizing assembly 10 generally comprises a spirometer 12 that has a mouthpiece 14 which can be placed in a user's mouth. The mouthpiece 14 has an outer wall 16 that has a plurality of intersecting sides 18 such that the mouthpiece 14 has a rectangular shape. The spirometer 12 may be a spirometer 12 of any conventional design that is commonly employed for measuring the lung capacity of a user.

A cover 20 is positionable around the mouthpiece 14 and the cover 20 is comprised of a fluid impermeable material to protect the mouthpiece 14 from contamination when the cover 20 is positioned around the mouthpiece 14. The cover 20 has a rear wall 22 and an outside wall 24 extending away from the rear wall 22, and the outside wall 24 has a top side 26, a bottom side 28, a first lateral side 30, a second lateral side 32 and a distal edge 34 with respect to the rear wall 22 defining an opening 36 into the cover 20. The outside wall 24 has an outside surface 38 and an inside surface 40, and the opening 36 insertably receives the mouthpiece 14 such that the inside surface 40 is directed toward the outer wall 16 of the mouthpiece 14.

The outside wall 24 has a bulbous portion 42 that is aligned with the distal edge 34. The bulbous portion 42 extends around each of the top side 26, the bottom side 28, the first lateral side 30 and the second lateral side 32. Furthermore, the bulbous portion 42 corresponding to the inside surface 40 compresses against the outer wall 16 of the mouthpiece 14 when the mouthpiece 14 is inserted into the opening 36. The cover 20 is comprised of a resiliently stretchable material thereby facilitating the opening 36 to conform to the shape of the mouthpiece 14 when the mouthpiece 14 is inserted into the opening 36.

A sterilizing unit 44 is integrated into the cover 20 and the sterilizing unit 44 emits ultraviolet radiation when the sterilizing unit 44 is turned on to kill microbes on the mouthpiece 14 thereby sterilizing the mouthpiece 14 between uses. In this way the mouthpiece 14 is inhibited from exposing a user to a respiratory infection when the user employs the spirometer 12. The sterilizing unit 44 comprises a plurality of light emitters 46 that is each integrated into the inside surface 40 of the outside wall 24 to emit light into an interior of the cover 20. Moreover, each of the light emitters 46 has an operational frequency corresponding to the frequency of ultraviolet radiation to kill bacteria and viruses. The plurality of light emitters 46 is positioned on a respective one of the top side 26 or the bottom side 28 of the outside wall 24 of the cover 20. Additionally, the light emitters 46 are spaced apart from each other and are distributed along an entire width of the respective top side 26 or bottom side 28. Each of the plurality of light emitters 46 may comprise a light emitting diode or other type of electronic light emitter.

A power button 48 is movably integrated into the outside surface 38 of the outside wall 24 of the cover 20 and the power button 48. The power button 48 is electrically coupled to each of the plurality of light emitters 46 for turning the plurality of light emitters 46 on an off. An indicator 50 is integrated into the outside wall 24 of the cover and the indicator 50 forms a continuous loop such that the indicator 50 extends around a full circumference of the power button 48. The indicator 50 emits a first color of light when the power button 48 is depressed to turn on the plurality of light emitters 46 to visually communicate that the light emitters 46 are turned on. Conversely, the indicator 50 emits a second color of light when the power button 48 is depressed to turn off the plurality of light emitters 46 to visually indicate that the light emitters 46 are turned off. The indicator 50 may comprise a light emitting diode or other type of electronic light emitter.

A power supply 52 is integrated into the cover 20, the power supply 52 is electrically coupled to the power button 48 and the power supply 52 comprises a rechargeable battery. A charge port 54 is recessed into the outside surface 38 of the outside wall 24 to insertably receive a charge cord 55. The charge port 54 is electrically coupled to the power supply 52 for charging the power supply 52. A charge indicator 56 is integrated into the outside surface 38 of the outside wall 24. The charge indicator 56 is electrically coupled to the power supply 52 and the charge indicator 56 emits light when the power supply 52 has been fully charged. The charge indicator 56 may comprise a light emitting diode or other type of electronic light emitter.

In use, the mouthpiece 14 is inserted into the cover 20 when the mouthpiece 14 is not being employed. The power button 48 is depressed to turn on the plurality of light emitters 46 thereby sterilizing the mouthpiece 14 while the mouthpiece 14 is positioned in the cover 20. In this way the mouthpiece 14 is inhibited from exposing the user to a potential respiratory infection or other infectious disease when the user employs the spirometer 12. The power button 48 is depressed to turn off the light emitters 46 and the mouthpiece 14 is removed from the cover 20 to facilitate the mouthpiece 14 to be employed. The charge cord 55 is plugged into the charge port 54 for charging the power supply 52 as needed.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A spirometer sterilizing assembly for sterilizing a mouthpiece of a spirometer, said assembly comprising:
   a spirometer having a mouthpiece wherein said mouthpiece is configured to be placed in a user's mouth;
   a cover being positionable around said mouthpiece, said cover being comprised of a fluid impermeable material wherein said cover is configured to protect said mouthpiece from contamination when said cover is positioned around said mouthpiece;
   a sterilizing unit being integrated into said cover, said sterilizing unit emitting ultraviolet radiation when said sterilizing unit is turned on wherein said sterilizing unit is configured to kill microbes on said mouthpiece to sterilize said mouthpiece between uses;
   wherein said mouthpiece has an outer wall has a plurality of intersecting sides such that said mouthpiece has a rectangular shape;
   wherein said cover has a rear wall and an outside wall extending away from said rear wall, said outside wall having a top side, a bottom side, a first lateral side, a second lateral side and a distal edge with respect to said rear wall defining an opening into said cover, said outside wall having an outside surface and an inside surface, said opening insertably receiving said mouthpiece such that said inside surface is directed toward said outer wall of said mouthpiece; and
   wherein said outside wall has a bulbous portion being aligned with said distal edge, said bulbous portion extending around each of said top side, said bottom side, said first lateral side and said second lateral side, said bulbous portion corresponding to said inside surface compressing against said outer wall of said mouthpiece when said mouthpiece is inserted into said opening.

2. The assembly according to claim 1, wherein said sterilizing unit comprises a plurality of light emitters, each of said light emitters being integrated into said inside surface of said outside wall wherein each of said light emitters is configured to emit light into an interior of said cover, each of said light emitters having an operational frequency corresponding to the frequency of ultraviolet radiation wherein each of said light emitters is configured to kill bacteria and viruses, said plurality of light emitters being positioned on a corresponding on of said top side or said bottom side of said outside wall of said cover, said light emitters being spaced apart from each other and being distributed along an entire width of said respective top side or said bottom side.

3. The assembly according to claim 2, wherein said sterilizing unit includes a power button being movably integrated into said outside surface of said outside wall of said cover, said power button being electrically coupled to each of said plurality of light emitters for turning said plurality of light emitters on an off.

4. The assembly according to claim 3, wherein said sterilizing unit includes an indicator being integrated into said outside wall of said cover, said indicator forming a continuous loop such that said indicator extends around a full circumference of said power button, said indicator emitting a first color of light when said power button is depressed to turn on said plurality of light emitters to visually communicate that said light emitters are turned on, said indicator emitting a second color of light when said power button is depressed to turn off said plurality of light emitters to visually indicate that said light emitter are turned off.

5. The assembly according to claim 3, wherein said sterilizing unit includes:
    a power supply being integrated into said cover, said power supply being electrically coupled to said power button, said power supply comprising a rechargeable battery;
    a charge port being recessed into said outside surface of said outside wall wherein said charge port is configured to insertably receive a charge cord, said charge port being electrically coupled to said power supply for charging said power supply; and
    a charge indicator being integrated into outside surface of said outside wall, said charge indicator being electrically coupled to said power supply, said charge indicator emitting light when said power supply has been fully charged.

6. A spirometer sterilizing assembly for sterilizing a mouthpiece of a spirometer, said assembly comprising:
    a spirometer having a mouthpiece wherein said mouthpiece is configured to be placed in a user's mouth, said mouthpiece having an outer wall having a plurality of intersecting sides such that said mouthpiece has a rectangular shape;
    a cover being positionable around said mouthpiece, said cover being comprised of a fluid impermeable material wherein said cover is configured to protect said mouthpiece from contamination when said cover is positioned around said mouthpiece, said cover having a rear wall and an outside wall extending away from said rear wall, said outside wall having a top side, a bottom side, a first lateral side, a second lateral side and a distal edge with respect to said rear wall defining an opening into said cover, said outside wall having an outside surface and an inside surface, said opening insertably receiving said mouthpiece such that said inside surface is directed toward said outer wall of said mouthpiece, said outside wall having a bulbous portion being aligned with said distal edge, said bulbous portion extending around each of said top side, said bottom side, said first lateral side and said second lateral side, said bulbous portion corresponding to said inside surface compressing against said outer wall of said mouthpiece when said mouthpiece is inserted into said opening, said cover being comprised of a resiliently stretchable material thereby facilitating said opening to conform to the shape of said mouthpiece when said mouthpiece is inserted into said opening;
a sterilizing unit being integrated into said cover, said sterilizing unit emitting ultraviolet radiation when said sterilizing unit is turned on wherein said sterilizing unit is configured to kill microbes on said mouthpiece to sterilize said mouthpiece between uses, said sterilizing unit comprising:
    a plurality of light emitters, each of said light emitters being integrated into said inside surface of said outside wall wherein each of said light emitters is configured to emit light into an interior of said cover, each of said light emitters having an operational frequency corresponding to the frequency of ultraviolet radiation wherein each of said light emitters is configured to kill bacteria and viruses, said plurality of light emitters being positioned on a respective one of said top side or said bottom side of said outside wall of said cover, said light emitters being spaced apart from each other and being distributed along an entire width of said respective top side of said bottom side;
    a power button being movably integrated into said outside surface of said outside wall of said cover, said power button being electrically coupled to each of said plurality of light emitters for turning said plurality of light emitters on an off;
    an indicator being integrated into said outside wall of said cover, said indicator forming a continuous loop such that said indicator extends around a full circumference of said power button, said indicator emitting a first color of light when said power button is depressed to turn on said plurality of light emitters to visually communicate that said light emitters are turned on, said indicator emitting a second color of light when said power button is depressed to turn off said plurality of light emitters to visually indicate that said light emitter are turned off;
    a power supply being integrated into said cover, said power supply being electrically coupled to said power button, said power supply comprising a rechargeable battery;
    a charge port being recessed into said outside surface of said outside wall wherein said charge port is configured to insertably receive a charge cord, said charge port being electrically coupled to said power supply for charging said power supply; and
    a charge indicator being integrated into said outside surface of said outside wall, said charge indicator being electrically coupled to said power supply, said charge indicator emitting light when said power supply has been fully charged.

* * * * *